(12) United States Patent
Kumoyama et al.

(10) Patent No.: US 7,762,984 B2
(45) Date of Patent: Jul. 27, 2010

(54) CATHETER

(75) Inventors: Kenichi Kumoyama, Shizuoka (JP); Junichi Kobayashi, Shizuoka (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 559 days.

(21) Appl. No.: 11/315,241

(22) Filed: Dec. 23, 2005

(65) Prior Publication Data
US 2006/0142696 A1 Jun. 29, 2006

(30) Foreign Application Priority Data
Dec. 28, 2004 (JP) .......................... 2004-381596

(51) Int. Cl.
*A61M 31/00* (2006.01)
*A61M 37/00* (2006.01)
*A61M 25/00* (2006.01)

(52) U.S. Cl. ..................... 604/103.04; 604/103.09; 604/525

(58) Field of Classification Search ............. 604/96.01, 604/103.1, 103.04, 264, 523, 528, 913, 915, 604/525, 103.09
See application file for complete search history.

(56) References Cited

U.S. PATENT DOCUMENTS

| | | | |
|---|---|---|---|
| 5,605,543 A * | 2/1997 | Swanson | 604/102.02 |
| 5,743,875 A * | 4/1998 | Sirhan et al. | 604/96.01 |
| 6,533,754 B1 * | 3/2003 | Hisamatsu et al. | 604/96.01 |
| 6,685,720 B1 * | 2/2004 | Wu et al. | 606/192 |
| 6,746,423 B1 * | 6/2004 | Wantink | 604/103.04 |
| 7,195,611 B1 * | 3/2007 | Simpson et al. | 604/103.04 |
| 7,294,124 B2 * | 11/2007 | Eidenschink | 604/525 |
| 2004/0092868 A1 * | 5/2004 | Murray, III | 604/103.04 |
| 2005/0049552 A1 * | 3/2005 | Holzapfel et al. | 604/103.04 |
| 2005/0267408 A1 * | 12/2005 | Grandt et al. | 604/103.04 |
| 2005/0277878 A1 * | 12/2005 | Lee | 604/103.04 |
| 2006/0270977 A1 * | 11/2006 | Fisher et al. | 604/103.04 |

FOREIGN PATENT DOCUMENTS

| | | |
|---|---|---|
| JP | 2001-95924 | 4/2001 |
| WO | WO 93/15786 | 8/1993 |
| WO | WO 95/28197 | 10/1995 |

* cited by examiner

*Primary Examiner*—Kevin C Sirmons
*Assistant Examiner*—Andrew M Gilbert
(74) *Attorney, Agent, or Firm*—Buchanan Ingersoll & Rooney PC

(57) ABSTRACT

A catheter includes a distal shaft, and a proximal shaft having its distal portion inserted and fixed in the distal shaft. The distal shaft includes a guide wire lumen, and a distal shaft lumen, with the distal shaft lumen communicating with a proximal shaft lumen. The proximal shaft includes a main body portion, a distal portion smaller in size than the main body portion and entering into the distal shaft lumen, and a proximal shaft inclined portion located between the main body portion and the distal portion. The distal shaft lumen has a lumen change portion reduced in lumen cross-section toward the distal side. The proximal shaft inclined portion and the lumen change portion abut on each other.

25 Claims, 13 Drawing Sheets

CATHETER

FIELD OF THE INVENTION

The present invention generally relates to a treatment or diagnosis catheter adapted to be inserted into a living organ such as a blood vessel, bile duct, windpipe, esophagus, urethra, and other organs. More specifically, the invention relates to a rapid exchange type catheter.

BACKGROUND DISCUSSION

One type of known of blood vessel insertion balloon catheter is a catheter used for PTCA (Percutaneous Transluminal Coronary Angioplasty), hereinafter referred to as a "PTCA catheter." In this catheter, a guide wire lumen for passing a guide wire therethrough is formed over the whole length of the catheter, in addition to the lumen for expanding a balloon. The catheter is inserted into a blood vessel in the condition where the guide wire is inserted in the guide wire passing lumen and the distal portion of the guide wire protrudes from the catheter.

To perform PTCA, a plurality of PTCA catheters differing in the outside diameter of the catheter shaft and in the outside diameter of the balloon in its expanded state are prepared. In some cases, catheter replacement is conducted after a first catheter is inserted into a blood vessel. The catheter replacement is preferably conducted while the guide wire is left indwelling in the blood vessel, from the viewpoint of reducing the burden on the patient, reducing operation time and labor, preventing infection, etc. In catheters referred to as rapid exchange type catheters, a port for insertion of the guide wire is formed not at the proximal end of the catheter but in a side surface on the distal side of the catheter. In this catheter, therefore, catheter replacement can be easily carried out while the guide wire is left indwelling in the blood vessel.

A known rapid exchange type catheter is disclosed in JP-A-Hei 6-507105 (WO 93/15786). In this catheter, to reinforce an insertion port for insertion and drawing-out of the guide wire, a reinforcing core wire is joined to a distal portion of a proximal shaft formed of a high-rigidity material such as a metal, and the core wire is extended to the distal side relative to the insertion port portion.

However, with the structure disclosed in JP-A-Hei 6-507105 (WO 93/15786), the core wire is processed as a member separate from the proximal shaft portion, and thereafter the processed core wire is joined to a distal portion of the proximal shaft portion by brazing or a like method. Thus, the assembling operation is intricate.

In view of this, Japanese Patent Laid-open No. 2001-95924 proposes a catheter in which a reinforcement portion is formed by reducing the diameter of a portion near the distal end of the proximal shaft to reinforce the insertion port portion with the reinforcement portion.

On the other hand, a catheter construction is disclosed in JP-A-Hei 10-503386 (WO 95/28197) in which the distal portion of the core wire is embedded in the tube wall of the shaft for the purpose of efficiently transmitting a pushing force exerted on the proximal shaft to the distal end of the catheter.

However, with the catheter disclosed in JP-A-Hei 10-503386 (WO 95/28197), a step of embedding the distal portion of the core wire into the tube wall is carried out after the step of inserting the core wire into the shaft. This thus requires a rather intricate manufacturing process.

SUMMARY

According to one aspect, a catheter comprises a distal shaft, and a proximal shaft having a distal portion inserted and fixed in the distal shaft. The distal shaft comprises a guide wire lumen and a distal shaft lumen, with the guide wire lumen extending in a longitudinal direction of the distal shaft and communicating with a guide wire insertion port at a proximal portion of the distal shaft, and the distal shaft lumen extending in the longitudinal direction of the distal shaft and communicating with a proximal shaft lumen formed inside the proximal shaft. The proximal shaft comprises a main body portion, a distal portion smaller in outer dimension than the main body portion and entering into the distal shaft lumen, and a proximal shaft inclined portion located between the main body portion and the distal portion. The distal shaft lumen possesses a lumen change portion that is reduced in lumen cross-section in a direction toward the distal side of the distal shaft lumen. The proximal shaft inclined portion and the lumen change portion abut each other so that a pushing force applied to the main body portion of the proximal shaft is transmitted to the distal shaft through the abutting proximal shaft inclined portion and lumen change portion.

According to another aspect, a catheter comprises a distal shaft and a proximal shaft. The distal shaft comprises a guide wire lumen and a distal shaft lumen which are separately disposed, with the guide wire lumen extending longitudinally along at least a portion of the distal shaft and terminating at a guide wire insertion port at a proximal end of the guide wire lumen, and with the distal shaft lumen extending longitudinally along at least a portion of the distal shaft. The proximal shaft is fixed to the distal shaft and comprises a proximal shaft lumen communicating with the distal shaft lumen. The proximal shaft comprises a main body portion, a distal portion and a proximal shaft inclined portion located axially between the main body portion and the distal portion. The distal portion of the proximal shaft possesses an outer dimension that is reduced relative to the main body portion, the distal portion of the proximal shaft is positioned inside the distal shaft lumen, and the proximal shaft inclined portion possesses an inclined surface that is inclined relative to a longitudinal axis of the proximal shaft. The distal shaft lumen comprises a lumen change portion possessing an inclined surface. The inclined surface of the proximal shaft inclined portion and the inclined surface of the lumen change portion axially overlap and abut one another so that a pushing force applied to the main body portion of the proximal shaft is transmitted to the distal shaft through the abutting inclined surfaces of the proximal shaft inclined portion and the lumen change portion.

With the catheter disclosed herein, a pushing force applied to the main body portion of the proximal shaft is transmitted to the distal shaft through the abutting portions. The catheter (e.g., a rapid exchange type catheter) is thus able to transmit a pushing force applied on the proximal side of the catheter to a distal portion of the catheter to provide a catheter having good pushability performance. In addition, the catheter can be manufactured by a comparatively simple process in which the proximal shaft is inserted into the lumen of the distal shaft from the proximal side until the proximal shaft inclined portion and the lumen change portion abut each other, with the distal shaft and the proximal shaft then being attached to each other.

BRIEF DESCRIPTION OF THE DRAWING FIGURES

The foregoing and additional features and characteristics of the disclosed subject matter will become more apparent from the following detailed description considered with reference to the accompanying drawing figures in which like reference numerals designate like elements.

DETAILED DESCRIPTION

Figure 1:
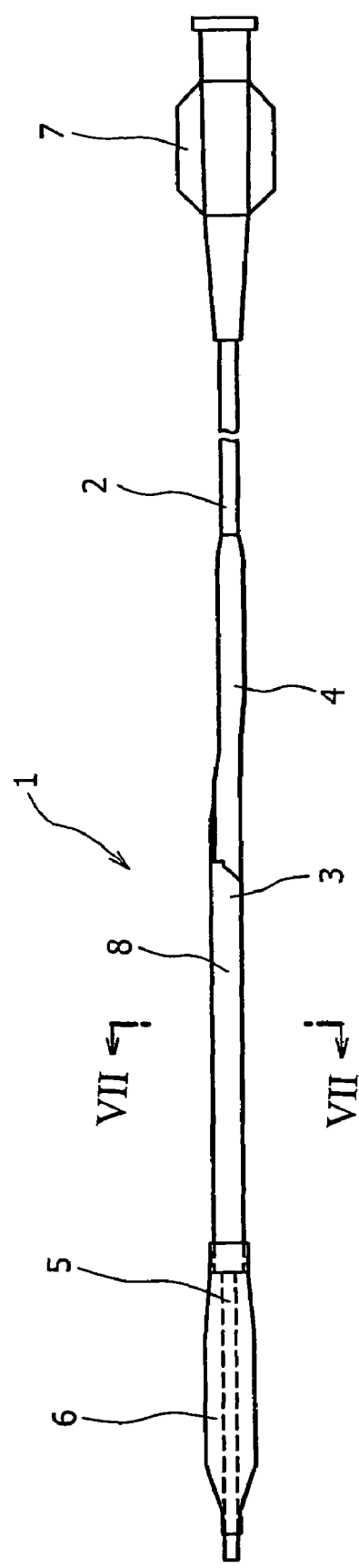
FIG. 1 is a front view showing an embodiment in which a catheter according to the present invention is applied to a PTCA catheter.

A catheter according to the present invention will now be described with reference to an embodiment shown in FIGS. 1-9 in which the catheter is applied to a PTCA catheter.

The catheter 1 according to an embodiment of the present invention comprises a distal shaft 3, and a proximal shaft 2 having its distal portion inserted and fixed in the distal shaft 3. The distal shaft 3 comprises a guide wire lumen 51 extending in the longitudinal direction of the distal shaft 3 and communicating with a guide wire insertion port 52 formed in a proximal portion of the distal shaft 3, and a distal shaft lumen 31 constituting a lumen different from the guide wire lumen 51 and formed in the longitudinal direction of the distal shaft 3. The distal shaft lumen 31 communicates with a proximal shaft lumen 20 formed in the proximal shaft 2.

The proximal shaft 2 comprises a main body portion 21, a distal portion 22 that is thinner or smaller in diameter than the main body portion 21 and entering into the distal shaft lumen 31, and a proximal shaft inclined portion 23 located between the main body portion 21 and the distal portion 22. The distal shaft lumen 31 has a lumen change portion 46 provided in the distal shaft 3 and reduced in lumen section (dimension of lumen section) toward the distal side, and the proximal shaft inclined portion 23 and the lumen change portion 46 abut on each other so that a pushing force applied to the main body portion 21 of the proximal shaft 2 is transmitted to the distal shaft 3 through the abutting portions.

Figure 2:
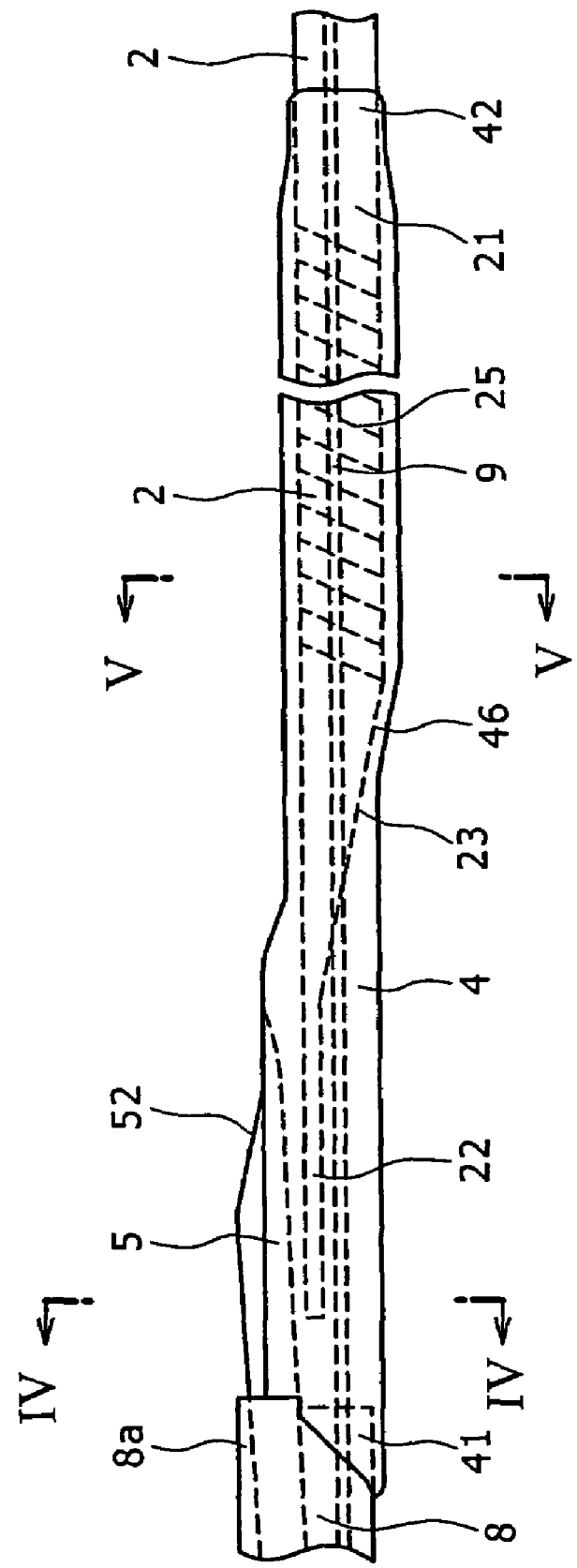
FIG. 2 is an enlarged view of the catheter shown in FIG. 1 in the vicinity of a joint portion between a distal shaft and a proximal shaft.
Figure 3:
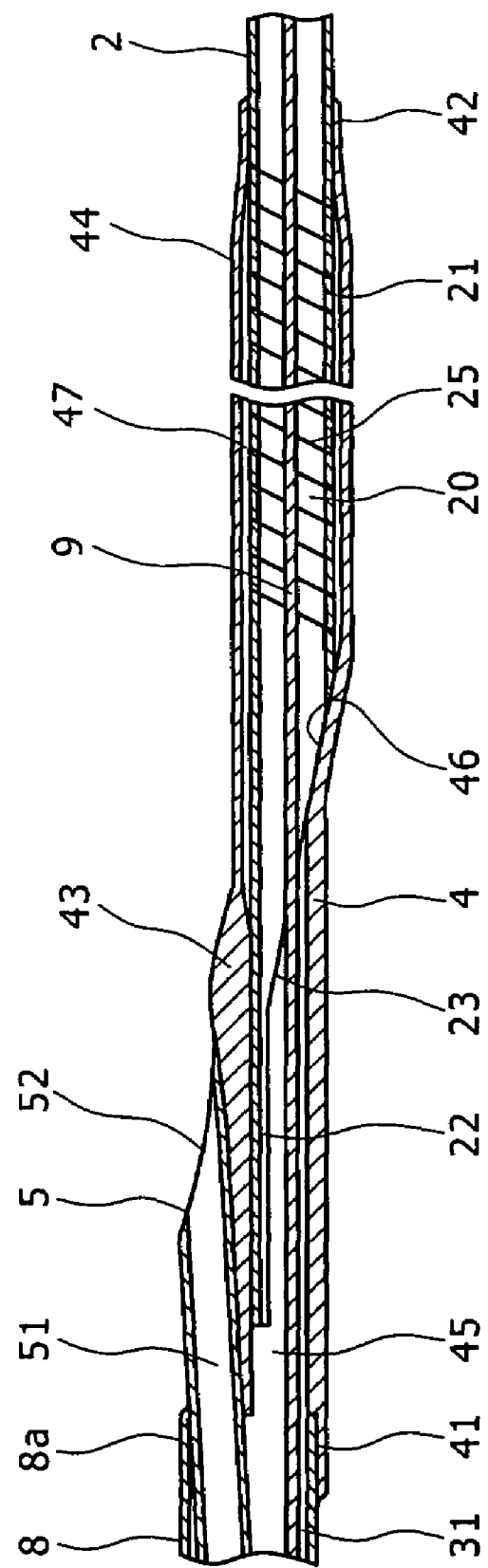
FIG. 3 is an enlarged cross-sectional view of the catheter shown in FIG. 1 in the vicinity of the joint portion between the distal shaft and the proximal shaft.

The catheter 1 according to the present invention is of the so-called rapid exchange type, and is composed of the distal shaft 3 and the proximal shaft 2 which are joined to each other by a fixing portion 42 as shown in FIGS. 1-3.

More specifically, in the catheter 1 according to this embodiment, the distal shaft 3 comprises an outer tube 8, an inner tube 5 and a connection tube portion 4. The inner tube 5 is disposed inside the outer tube 8, is fixed to the outer tube 8 at its proximal portion and includes the guide wire insertion port 52 at its proximal portion. The connection tube portion 4 is disposed side by side with the proximal portion of the inner tube 5, is fixed to the proximal portion of the inner tube 5 and has its distal portion fixed in a liquid-tight manner to a proximal portion of the outer tube 8. The proximal shaft 2 has its distal portion inserted and fixed in the connection tube portion 4 of the distal shaft 3, wherein a distal shaft lumen 31 defined between the inside surface of the outer tube 8 or the connection tube portion 4 and the outside surface of the inner tube 5 is communicated with a proximal shaft lumen 20 formed in the proximal shaft 2. Furthermore, the proximal shaft 2 comprises the main body portion 21, the distal portion 22 smaller in diameter (or thinner) than the main body portion 21 and entering into the lumen 45 of the connection tube portion 4, and the proximal shaft inclined portion 23 located between the main body portion 21 and the distal portion 22. The lumen 45 of the connection tube portion 4 has a lumen change portion 46 provided on the proximal side of the connection tube portion 4 and reduced in lumen cross-section toward the distal side. The proximal shaft inclined portion 23 and the lumen change portion 46 abut on each other so that a pushing force applied to the main body portion 21 of the proximal shaft 2 is transmitted to the distal shaft 3 through the abutting portions. That is, an inclined surface of the proximal shaft inclined portion 23 and an inclined surface of the lumen change portion 46 axially overlap one another and abut each other so that a pushing force applied to the main body portion 21 of the proximal shaft 2 is transmitted to the distal shaft 3 through the abutting surfaces.

The distal shaft 3 comprises the outer tube 8, the inner tube 5 and the connection tube portion 4 as shown in FIGS. 1-3. More specifically, the distal shaft 3 comprises the outer tube 8, the inner tube 5 disposed inside the outer tube 8 and fixed to the outer tube 8 at its proximal portion, and the connection tube portion 4 disposed side by side with the proximal portion of the inner tube 5, fixed to the proximal portion of the inner tube 5 and having its distal portion fixed in a liquid-tight manner to the proximal portion of the outer tube 8. The outer tube 8 and the connection tube portion 4 fixed to the proximal portion of the outer tube 8 are not limited to the configuration in which the two members are thus fixed. That is, by way of example, the outer tube 8 and the connection tube portion 4 may be composed of a single member.

The outer tube 8 is a tube body opening from the distal end to the proximal end thereof so that the inner tube 5 can be inserted in the inside thereof. The outer tube 8 has an outside diameter of 0.6 to 1.5 mm, preferably 0.8 to 1.1 mm, and an inside diameter of 0.5 to 1.4 mm, preferably 0.7 to 1.0 mm.

Figure 9:
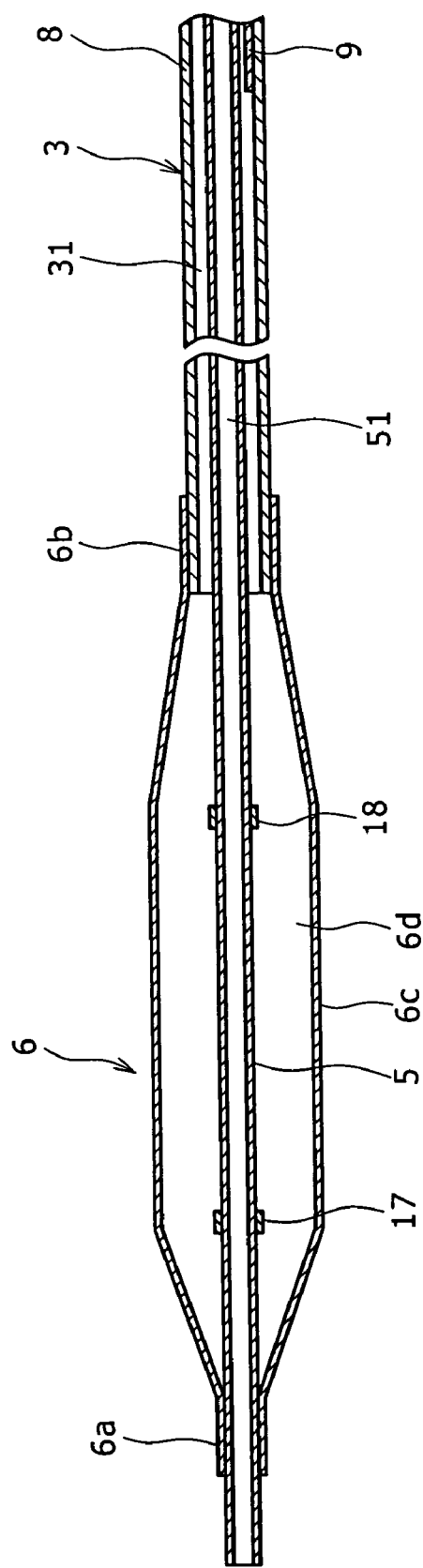
FIG. 9 is an enlarged cross-sectional view of a distal portion of the catheter shown in FIG. 1.

As shown in the drawing figures, the inner tube 5 is a tube body having the guide wire lumen 51 opening from the distal end to the proximal end thereof, and is inserted in the outer tube 8. In addition, a distal portion of the inner tube 5 protrudes by a predetermined length from the distal end of the outer tube 8 as shown in FIG. 9. The inner tube 5 has an outside diameter of 0.35 to 1.0 mm, preferably 0.45 to 0.8 mm, and an inside diameter of 0.2 to 0.9 mm, preferably 0.35 to 0.7 mm. The protrusion length of the inner tube 5 from the distal end of the outer tube 8 differs depending on the length of a balloon used, and is about 5 to 100 mm, preferably 10 to 60 mm.

Figure 5:
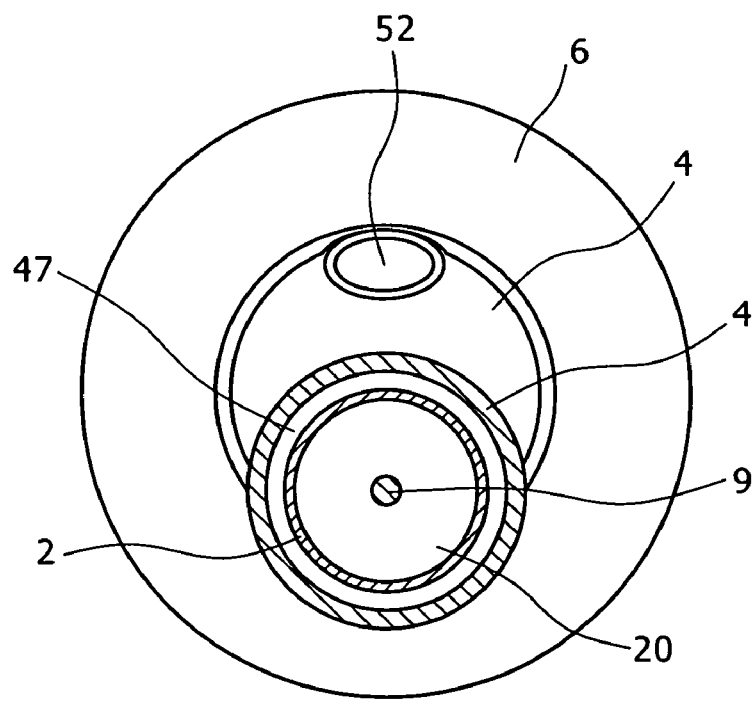
FIG. 5 is a cross-sectional view along the section line V-V of FIG. 2.

In addition, the inner tube 5 has its proximal portion exposed out of the outer tube 8 as shown in FIGS. 2 and 3. The inner tube 5 is fixed in a liquid-tight manner to the proximal end of the outer tube 8 at a portion of the inner tube slightly on the distal side of the proximal end of the inner tube 5. The proximal portion of the inner tube 5 (in this embodiment, the proximal end of the inner tube 5) is provided with the guide wire insertion port 52. As shown in FIGS. 2, 3 and 5, the guide wire insertion port 52 is formed in an oblique shape so as to incline toward the proximal side. This helps facilitate insertion of a guide wire.

As shown in FIGS. 2 and 3, the connection tube portion 4 has its distal portion formed obliquely. In the illustrated embodiment, the distal portion 41 of the connection tube portion 4 does not enter the outer tube 8, but is located on the outside of the outer tube 8. A part of the inside surface of the distal portion 41 of the connection tube portion 4 is in contact with a part of the outside surface of the proximal portion of the outer tube 8. The outer tube 8 and the connection tube portion 4 are fused in a liquid-tight manner to each other at the contact surface. Further, a part of the outside surface on the distal side of the connection tube portion 4 is in contact with a part of the outside surface of the proximal portion of the inner tube 5. The inner tube 5 and the connection tube portion 4 are fused in a liquid-tight manner to each other at the contact portion 43. In addition, the contact portion 43 is formed through fusion in a shape corresponding to the curved shape of a proximal portion of the inner tube 5, and constitutes an inclined surface contiguous with the guide wire insertion port 52 of the inner tube 5.

In the catheter 1 of this embodiment, the proximal portion of the connection tube portion 4 and the distal portion of the proximal shaft 2 are fused to each other. A connection tube portion lumen 45 defined between the inside surface of the connection tube portion 4 and the outside surface of the inner tube 5 communicates with a proximal shaft lumen 20 defined inside the proximal shaft 2.

The materials constituting the inner tube 5, the connection tube portion 4, and the outer tube 8 are preferably materials having a certain degree of flexibility. Examples of preferred materials include thermoplastic resins such as polyamides, polyesters, polyamide elastomers, polyester elastomers, polyolefins (e.g., polyethylene, polypropylene, ethylene-propylene copolymer, ethylene-vinyl acetate copolymer, and crosslinked or partly crosslinked products thereof), polyvinyl chloride, polyurethane, etc. The inner tube 5 may be formed of a single resin material. To provide good slidability of the guide wire, however, it is preferable that an inner layer of the inner tube 5 is formed of a low-friction material, for example, polyethylene or fluoro-resin, and an outer layer of the inner tube 5 is formed of a material compatible with the material(s) of the distal shaft (the outer tube 8 and the connection tube portion 4). In this case, the inner layer forming material may be incompatible with the materials of the proximal shaft and the distal shaft.

Figure 8:
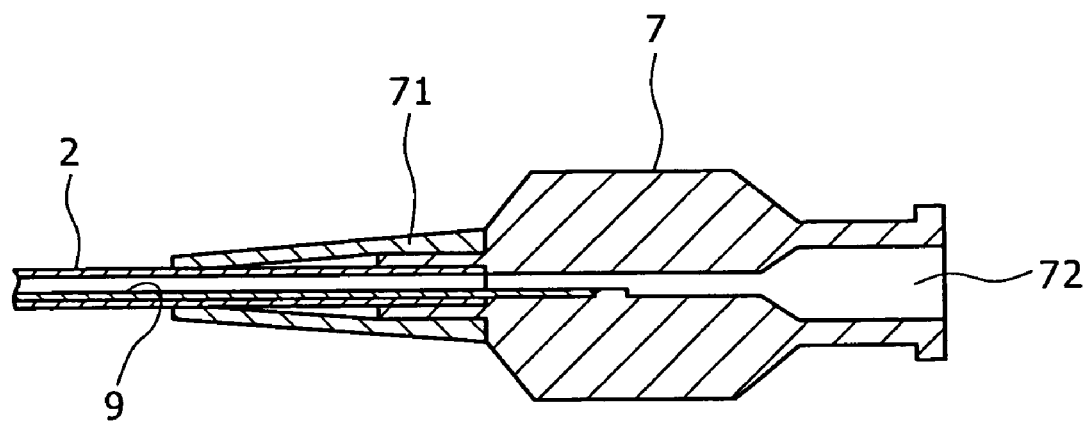
FIG. 8 is an enlarged sectional view of a proximal portion of the catheter shown in FIG. 1.

As shown in FIGS. 2 to 5 and FIG. 8, the proximal shaft 2 is a tube body opening from the distal end to the proximal end thereof. As shown in FIG. 8, the proximal shaft 2 is provided with a hub 7 fixed to the proximal end thereof. A distal portion of the proximal shaft 2 is joined to a proximal portion of the distal shaft 3.

The proximal shaft 2 is fixed to a distal portion of the hub 7 at the proximal end thereof. A kink-preventive tube 71 is attached to the outside surface of a boundary portion between the hub 7 and the proximal shaft 2 so as to cover both of the members. In addition, a proximal portion of the hub 7 constitutes a connection portion 72 for connection to a balloon expanding fluid injecting implement (for example, syringe).

The proximal shaft 2 has a length of 800 to 1500 mm, preferably 1000 to 1300 mm, an outside diameter of 0.5 to 1.5 mm, preferably 0.6 to 1.3 mm, and an inside diameter of 0.3 to 1.4 mm, preferably 0.5 to 1.2 mm.

Figure 6:
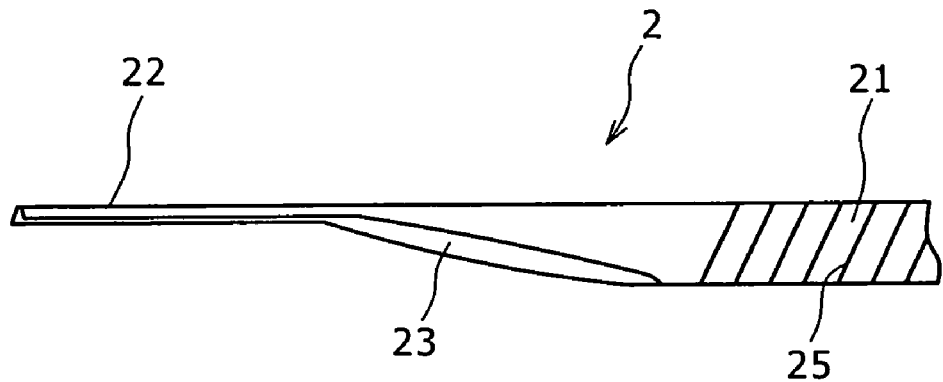
FIG. 6 is a perspective view of a distal portion of the proximal shaft used in the catheter of FIG. 1.
Figure 7:
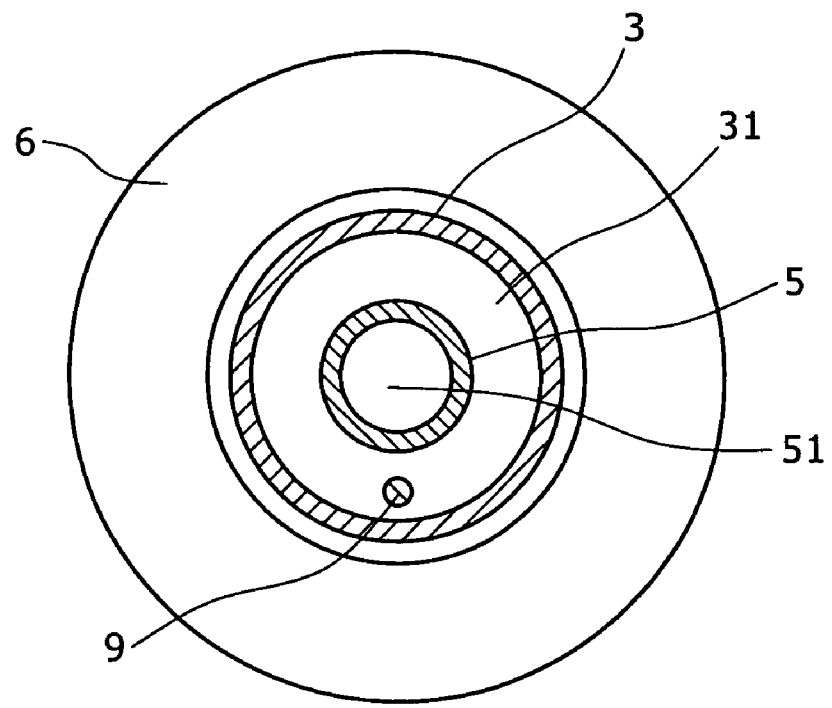
FIG. 7 is a cross-sectional view along the section line VII-VII of FIG. 1.

As illustrated in FIG. 6 and described previously, the proximal shaft 2 includes the main body portion 21, the distal portion 22 smaller in diameter (or thinner) than the main body portion 21 and entering into the lumen 45 of the connection tube portion 4, and the proximal shaft inclined portion 23 connecting the main body portion 21 and the distal portion 22. The length of the distal portion 22 is preferably about 3 to 15 mm. The length in the axial direction of the inclined portion 23 is preferably about 2 to 10 mm.

Figure 4:
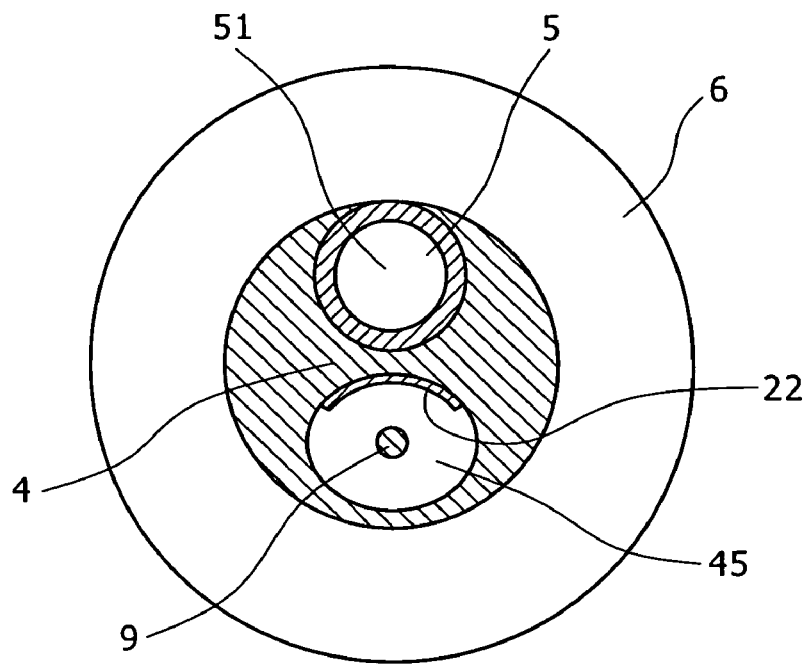
FIG. 4 is a cross-sectional view along the section line IV-IV of FIG. 2.

As shown in FIGS. 3, 4 and 6, the distal portion 22 of the proximal shaft 2 is formed in a trough shape as if it were formed by extending only a part of the main body portion 21 of the proximal shaft 2 in the axial direction. The size of the arc in the trough-shape portion formed by the cross-section obtained by cutting the distal portion 22 in a direction orthogonal to the axial direction of the distal portion 22 is preferably about $\frac{1}{16}$ to $\frac{1}{2}$ times the size of the circle formed by the cross-section of the main body portion 21. That is, the circumferential extent of the trough shaped distal portion 22 is preferably about $\frac{1}{16}$ to $\frac{1}{2}$ times the circumferential extent of main body portion 21.

The distal portion of the proximal shaft 2 is not limited to a trough shape that is curved in the direction of the center axis of the shaft 2 as shown in FIG. 4, as it may possess a trough shape that is curved in the direction opposite to the direction of the center axis of the shaft or in a flat plate-like shape.

The proximal shaft inclined portion 23 is so formed as to be angled relative to the center axis of the proximal shaft 2 over the range from the distal end of the main body portion 21 to the proximal end of the distal portion 22. In this proximal shaft 2, the proximal shaft inclined portion 23 is in a form as if it were obtained by obliquely cutting the proximal shaft 2 over a predetermined length, and the thus cut-out inclined portion constitutes a communication portion for communication between the proximal shaft lumen 20 and the distal shaft lumen 31. In other words, the distal portion 22 of the proximal shaft 2 possesses a form as if it were obtained by cutting out the proximal shaft 2 over a predetermined length and a predetermined width in the axial direction, while the proximal shaft inclined portion 23 possesses a form as if it were obtained by obliquely cutting out the proximal shaft 2 over a predetermined length, with the cut-out inclined portion 23 constituting the communication portion for communication between the proximal shaft lumen 20 and the distal shaft lumen 31. With the inclined portion as a whole set to be an opening in this manner, relatively good the flow or distribution of a fluid injected into the proximal shaft lumen 20 can be obtained. It is to be understood that the inclined portion 23 may be so formed that only the distal portion thereof is opened and the proximal portion thereof is not opened.

The distal portion of the proximal shaft 2 may be cut into a shape in which the width of the distal portion is reduced toward the distal side.

As a material constituting the proximal shaft 2, a material which is comparatively high in rigidity, for example, a metal such as Ni—Ti, brass, SUS, aluminum, etc., is preferably used. Resins such as polyimides, polyvinyl chloride, polycarbonates, etc. may also be used inasmuch as the resin has a comparatively high rigidity.

In the catheter 1 according to this embodiment, the lumen 45 of the connection tube portion 4 constitutes a proximal portion of the distal shaft lumen 31, and the lumen change portion 46 is provided inside the connection tube portion 4. The distal portion 22 of the proximal shaft 3 is positioned so as to enter the connection tube portion lumen 45.

The connection tube portion 4 is in the form shown in FIGS. 2-4 in which the connection tube portion 4 is provided at its distal portion with the fixing portion (distal portion) 41 for fixation to the outer tube 8, and a part of the side wall on the proximal side relative to the fixing portion 41 includes the fused portion (contact portion) 43 fused in a liquid-tight manner to a part of the side wall of the proximal portion of the inner tube 5. The connecting tube also includes the lumen change portion 46 located on the proximal side relative to the fused portion 43, a tubular portion 44 contiguous with the lumen change portion 46 and extending over a predetermined length, and a fixing portion 42 formed at the proximal end for fixation to the proximal shaft 2.

In this embodiment, the distal portion of the lumen 45 inside the connection tube portion 4 is in a side-by-side relationship with the inner tube 5, and the lumen 45 is present alone on the proximal side relative to the proximal end of the inner tube 5. The lumen 45 in the area where the inner tube 5 is absent is provided with the lumen change portion 46 in which the lumen cross-section is reduced toward the distal side as shown in FIG. 3. In this embodiment, the lumen 45 inside the connection tube portion 4 is smaller in inside diameter on the distal side than on the proximal side of the lumen change portion (lumen inclined portion or inclined portion of the distal shaft) 46. In the present invention, however, the lumen change portion 46 is not limited to such a shape. For example, the lumen change portion includes configurations in which a wall portion is formed in the direction perpendicular to the major axis of the connection tube portion 4, whereby the distal side relative to the wall portion is narrower than the proximal side relative to the wall portion. In other words, the lumen change portion 46 may be either one of a lumen stepped portion and a lumen inclined portion. In this embodiment, the outside surface of the connection tube portion 4 corresponding to the lumen change portion 46 is also inclined according to the inclined surface of the lumen change portion 46 as seen in FIG. 3. Thus, the lumen change portion 46 is located on the proximal side relative to the area where both the distal shaft lumen (connection tube portion lumen) 31 and the inner tube lumen are present, on the distal side relative to the guide wire insertion port 52, whereby the inside diameter of the distal shaft lumen 31 in the area where the two lumens coexist can be made smaller. Thus, the outside diameter of the portion where the two lumens coexist can be restrained from being excessively large.

As described above, the proximal shaft inclined portion 23 of the proximal shaft 2 and the lumen change portion 46 of the connection tube portion 4 abut each other. This ensures that a pushing force applied to the main body portion 21 of the proximal shaft 2 is transmitted to the distal shaft 3 through the abutting portions of the two members 2, 4. As shown in FIG. 3, in this embodiment, the proximal shaft 2 is located at the proximal portion of the connection tube portion 4 so that the distal portion 22 of the proximal shaft 2 is located on the side of the fused portion 43 and the inner tube 5. The distal portion 22 of the proximal shaft 2 may make contact with the fused portion 43 (and the inner tube 5), or may be slightly spaced from the latter. Preferably, the distal portion 22 of the proximal shaft 2 is in contact with the fused portion 43 (and the inner tube 5). Furthermore, as shown in FIGS. 2 and 3, the distal end of the distal portion 22 of the proximal shaft 2 is preferably located on the distal side (with respect to the catheter 1) relative to the guide wire insertion port 52. This ensures that the guide wire insertion port 52 is reinforced, and the catheter 1 can be prevented from kinking in the vicinity of the port 52. In addition, as shown in FIGS. 2 and 3, it is preferable that the distal end of the distal portion 22 of the proximal shaft 2 does not reach the outer tube 8 (i.e., does not extend so far axially that the distal end of the distal portion 22 axially overlaps with the outer tube 8).

In this embodiment, the direction of the guide wire insertion port 52 of the inner tube 5 and the direction of the proximal shaft inclined portion 23 are opposite to each other with respect to the center axis of the outer tube 8. In other words, in this embodiment, the port 52 is present on the back side of the arc in the cross section of the proximal shaft inclined portion 23 (the outside of the curvature of the inclined portion 23 or the outer side of the inclined portion 23). This helps ensure that the catheter is restrained from being bent at the time of inserting the guide wire in the guide wire lumen 51 and that the catheter can be favorably prevented from kinking or bending in the vicinity of the guide wire insertion port 52. When the guide wire is inserted in the guide wire lumen 51, the catheter is liable to be curved in such a direction that the guide wire is located on the outside of curvature. When such a curving has occurred, the pushing force exerted by the hand is liable to be relieved or lost. However, in the area where the proximal shaft inclined portion 23 is provided, it is difficult for the catheter to be curved in such a direction that the proximal shaft inclined portion 23 is located on the inside of curvature. The catheter can thus be restrained or prevented from being curved at the time of insertion of the guide wire.

As described above and shown in FIG. 3, the distal portion 22 of the proximal shaft 2 possesses a trough shape as if it were formed by extending only a part of the main body portion 21 of the proximal shaft 2 in the axial direction. The outside of the curvature of the distal portion 22 is so disposed as to be located on the side of the fused portion 43 and the inner tube 5 in the lumen 31. Therefore, the trough-shaped distal portion 22 is in the state of directing its back (the outside of the curvature thereof) to the fused portion 43 and the inner tube 5, whereby the catheter is more securely restrained or prevented from being curved at the time of insertion of the guide wire.

Incidentally, this curving-resistant effect may be produced in other types of catheters that do not include any abutting contact between the proximal shaft inclined portion 23 and the lumen change portion 46.

The distal portion of the main body portion 21 of the proximal shaft 2 may be provided with a slit 25 or a multiplicity of openings as shown in FIGS. 3 and 6. It is preferable that the region where the slit or openings are formed has its distal end slightly on the proximal side relative to the proximal shaft inclined portion 46 and extends over a predetermined length to the proximal side. It is to be appreciated that the proximal shaft inclined portion 23 may also be provided with a slit or openings. The axial length of the region where the slit or openings are formed is preferably about 100 to 300 mm. With such slit or openings provided, relatively rapid variations in the physical properties of the distal portion of the main body portion 21 of the proximal shaft 2 are significantly reduced or eliminated, and the catheter can be prevented from kinking and can be easily deformed (curved).

The slit 25 is preferably a spiral slit as shown in the figures, but may be a slit extending in parallel to the center axis of the shaft 2. In addition, where the slit is a spiral slit, the pitch of the slit may be appropriately changed along the longitudinal direction of the proximal shaft 2 to thereby provide a variation in flexibility. Besides, the pitch of the spiral slit is preferably smaller on the distal side of the slit and larger on the proximal side of the slit. This helps ensure that the flexibility increases toward the distal portion, rapid variation in physical properties is generally avoided, and natural curvature is achieved. In addition, it is preferable that, the pitch at an intermediate portion between the distal portion and the proximal portion is set between the pitch at the distal portion and the pitch at the proximal portion or is gradually varied. Particularly, it is preferable that the spiral slit has a pitch gradually decreasing toward the distal end or has a width gradually increasing toward the distal end.

In the case where openings are provided in place of the slit, the diameter of the openings is preferably about 0.1 to 0.4 mm, more preferably 0.2 to 0.3 mm. Besides, the diameter of the openings is preferably about 1/10 to 1/3 times the outside diameter of the proximal shaft 2. The interval between the openings is preferably about 0.1 to 0.5 mm. The shape of the openings may not necessarily be a true circle, and may be, for example, an ellipse, an oblong shape elongated in the circumferential direction or the axial direction of the proximal shaft 2, a polygon (e.g., tetragon, pentagon) or the like. The number of the openings is preferably greater on the distal side than on the proximal side in the region where the openings are provided. Furthermore, it is preferable that the number of openings gradually increases along the direction from the proximal side toward the distal side.

In this embodiment, the distal portion of the main body portion 21 of the proximal shaft 2 is provided with a slit or a multiplicity of openings, a proximal portion of the distal shaft 3 envelops the main body portion 21 of the proximal shaft 2 provided with the slit or multiplicity of openings, and the proximal portion of the distal shaft 3 is attached to the proximal shaft 2 on the proximal side relative to the area where the slit or multiplicity of openings are formed. Specifically, the connection tube portion 4 has a tubular portion 44 for enveloping the region where the slit or openings are formed in the proximal shaft 2. The fixing portion 42 of the connection tube portion 4 is fixed in a liquid-tight manner to the proximal shaft 2 on the proximal side relative to the region where the slit or openings are formed. Further, as shown in FIGS. 3 and 5, a spacing (gap) 47 is defined between the outer surface of the proximal shaft 2 and the inner surface of the tubular portion 44 of the connection tube portion 4, in other words between the proximal shaft 2 and the distal shaft 3 enveloping the region where the slit or openings are formed in the proximal shaft 2. Stated differently, the tubular portion 44 of the connection tube portion 4 (the distal shaft 3) is not in close contact with the proximal shaft 2. Therefore, deformation of the region where the slit or openings are formed of the proximal shaft 2 is not significantly hindered by the tubular portion 44, and favorable curving is possible.

The overall length of the connection tube portion 4 is preferably about 100 to 400 mm. In addition, the length from the distal end of the connection tube portion 4 to the proximal end of the lumen change portion 46 is preferably about 3 to 15 mm, more preferably 5 to 7 mm. The length of the tubular portion 44 of the connection tube portion 4 is preferably about 50 to 300 mm.

In this embodiment, considering that the connection tube portion 4 covers the somewhat long slit portion of the proximal shaft 2, the connection tube portion 4 is somewhat long, and the lumen change portion (lumen inclined portion) 46 is located on the distal side of the connection tube portion 4. However, variations on this configuration are possible in that, for example, the lumen change portion 46 may be located on the proximal side of the connection tube portion 4.

A rigidity-imparting body 9 may also be inserted in the proximal shaft 2 as shown in FIGS. 2-5 and 8. In the illustrated embodiment, this rigidity-imparting body 9 is fixed to the hub 7 of the proximal shaft 2 at its proximal portion, and the distal end of the rigidity-imparting body 9 protrudes beyond the distal end of the proximal shaft 2 and extends into the inside of the distal shaft 3. In this embodiment, the distal portion of the rigidity-imparting body 9 reaches the inside of the distal shaft lumen 31 defined between the inner tube 5 and the outer tube 8 of the distal shaft 3 (i.e., the balloon expanding lumen).

As mentioned, the rigidity-imparting body 9 extends inside the proximal shaft 2 from the proximal end of the proximal shaft 2 toward the distal side. In addition, to avoid hindering the curving of the catheter 1, the rigidity-imparting body 9 has only its proximal portion fixed to the proximal shaft 2 or the hub 7, and the remainder of the rigidity-imparting body 9 is not fixed to any other portion of the inside of the proximal shaft 2 (exclusive of the proximal portion of the proximal shaft 2), the inner tube 5 and the distal shaft 3. The rigidity-imparting body 9 prevents extreme bending of the proximal shaft 2 and meandering of the proximal shaft 2 in a blood vessel, without considerably lowering the flexibility of the proximal shaft 2. The rigidity-imparting body 9 is preferably composed of a filamentous body. The filamentous body is preferably a metallic wire, formed of, for example, an elastic metal or superelastic alloy, such as stainless steels, and most preferably spring high tensile strength steel or superelastic alloy wires, with the wire diameter being 0.05 to 1.5 mm, preferably 0.1 to 1.0 mm.

Superelastic alloys here refer to those alloys which are generally called shape memory alloys and show superelasticity at least at the living body temperature (around 37° C.). Particularly preferred superelastic alloys for use here include Ti—Ni alloy containing 49-53 atm % of Ni, Cu—Zn alloy containing 38.5-41.5 wt % of Zn, Cu—Zn—X alloys containing 1-10 wt % of X (X=Be, Si, Sn, Al, or Ga), and Ni—Al alloy containing 36-38 atm % of Al. Particularly preferred is the Ti—Ni alloy. The mechanical properties of the alloy can be changed, as required, by substituting a part of the Ti—Ni alloy by 0.01-10.0 atm % of X to obtain a Ti—Ni—X alloy (X=Co, Fe, Mn, Cr, V, Al, Nb, W, B or the like) or substituting a part of the Ti—Ni alloy by 0.01-30.0 atm % of X to obtain a Ti—Ni—X alloy (X=Cu, Pb, or Zr), or by selecting the cold working ratio and/or the final heat treatment conditions.

In addition, the catheter in this embodiment is a so-called balloon catheter, wherein the catheter 1 has a balloon 6 possessing a distal portion and a proximal portion which are attached to a distal portion of the distal shaft 3, and which can be expanded by fluid flowing into the distal shaft lumen 31.

As shown in FIG. 9, the balloon 6 has a distal joint portion 6a and a proximal joint portion 6b, the distal joint portion 6a is fixed to the inner tube 5 at a position slightly on the proximal side relative to the distal end of the inner tube 5, and the proximal joint portion 6b is fixed to a distal portion of the outer tube 8. In addition, the balloon 6 communicates with the distal shaft lumen (balloon expanding lumen) 31 in the vicinity of a proximal portion thereof. The balloon 6 may be collapsed or folded at the circumference of the inner tube 5 when it is not expanded. The balloon 6 has a constant-diameter tubular portion (preferably, hollow cylindrical portion) 6c. The roughly hollow cylindrical portion may not necessarily be a true hollow cylinder, and may be in the shape of a column with a polygonal base. As has been mentioned above, the distal joint portion 6a is attached in a liquid-tight manner to the inner tube 5, and the proximal joint portion 6b is attached in a liquid-tight manner to the distal end of the distal shaft 3. This attachment can be achieved by use of an adhesive or by thermal fusing. As shown in FIG. 9, the balloon 6 forms an expansion space 6d between the inside surface of the balloon 6 and the outside surface of the inner tube 5. The expansion space 6d is communicated with the expanding lumen 31 along the entire circumference thereof, at a proximal portion thereof. Since the proximal end of the balloon 6 is thus communicated with the expanding lumen 31 having a comparatively large inside volume, it is possible to ensure injection of an expanding fluid into the balloon 6 via the expanding lumen 31.

The material for forming the balloon 6 is preferably a material having a certain degree of flexibility, and examples of materials which can be used include thermoplastic resins such as polyolefins, polyvinyl chloride, polyamides, polyamide elastomers, polyester elastomers, polyurethane, polyesters, polyarylene sulfides, etc., silicone rubbers, and latex rubber. Particularly, stretchable (orientable) materials are preferred, and the balloon 6 is preferably formed of a biaxially oriented material having high strength and tensile strength. As for the size of the balloon 6, the hollow cylindrical portion (expandable portion 6c) in its expanded state has an outside diameter of 1.5 to 5.0 mm, preferably 2.5 to 4.0 mm, and a length of 5 to 50 mm, preferably 10 to 40 mm. In addition, the distal joint portion 6a has an outside diameter of 0.5 to 1.5 mm, preferably 0.7 to 1.0 mm, and a length of 1 to 5 mm, preferably 1.0 to 1.3 mm. Besides, the proximal joint portion 6b has an outside diameter of 0.8 to 1.6 mm, preferably 1.0 to 1.5 mm, and a length of 1 to 5 mm, preferably 2 to 4 mm. The material constituting the balloon 6 may be a multi-layer material or a blend of the above-mentioned materials.

A distal contrast marker 17 is fixed to the outside surface of the inner tube 5 at a position in the vicinity of the distal end of the hollow cylindrical portion 6c of the balloon 6. Similarly, a proximal contrast marker 18 is fixed to the outside surface of the inner tube 5 at a position in the vicinity of the proximal end of the interior of the hollow cylindrical portion 6c of the balloon 6. The contrast markers are preferably formed of a radiopaque material (for example, gold, platinum, tungsten, or an alloy thereof, or a silver-palladium alloy or the like). This makes it possible to confirm the positions of the distal end and the proximal end of the hollow cylindrical portion 6c of the balloon 6 by radiography.

In addition, the catheter according to the present invention is not limited to the PTCA catheter as in the above-described embodiment. For example, the catheter is also applicable to a living organ expanding catheter, an imaging catheter, a drug injecting catheter, an ultrasonic catheter or the like. As a living organ expanding catheter, for example, a catheter can be considered which has substantially the same configuration as that of the above-described PTCA catheter and which is provided on a balloon with a stent capable of being expanded by the balloon.

Figure 10:
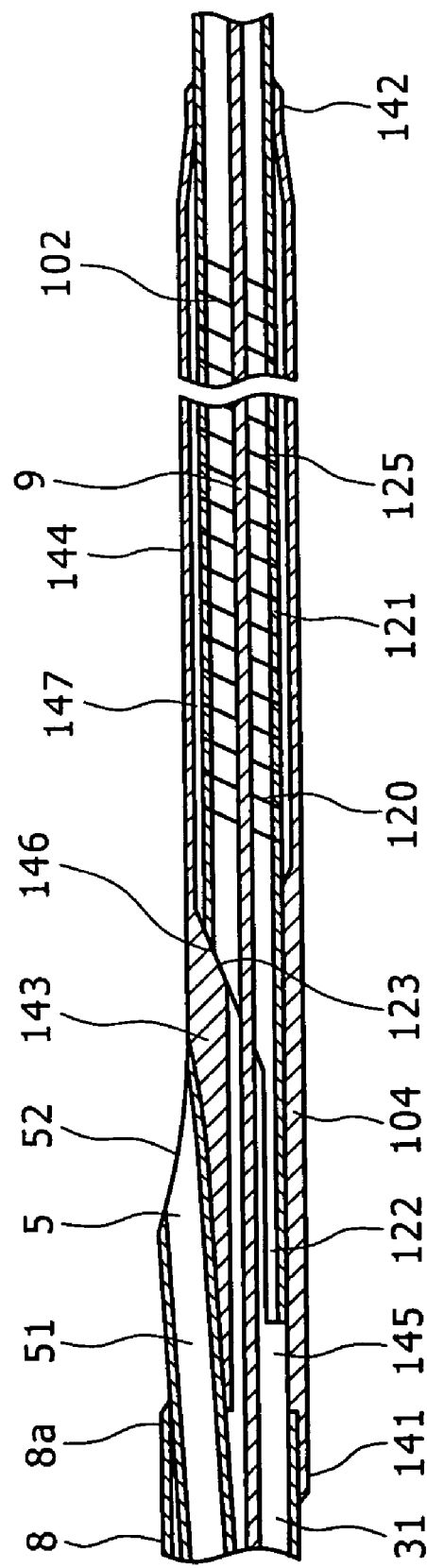
FIG. 10 is an enlarged cross-sectional view of the vicinity of a joint portion between a distal shaft and a proximal shaft in another embodiment of the catheter according to the present invention.
Figure 11:
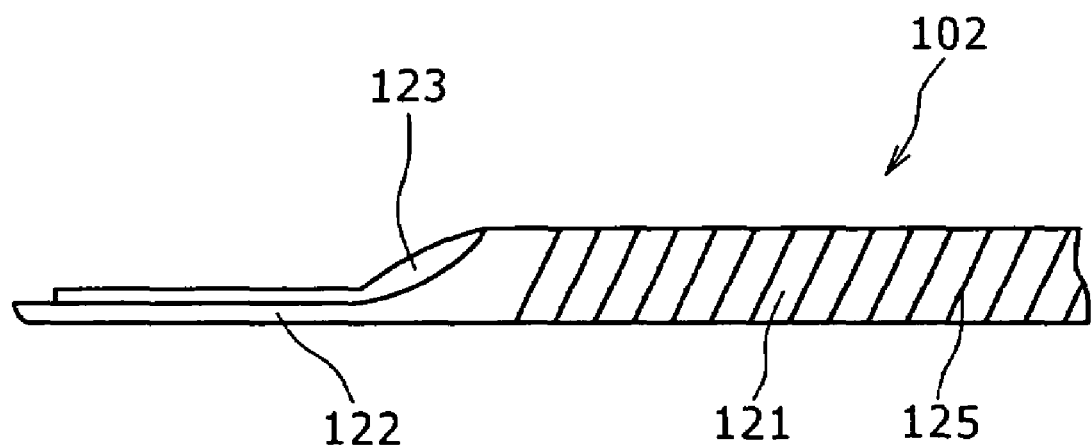
FIG. 11 is a perspective view of a distal portion of a proximal shaft used in the catheter shown in FIG. 10.

The connection tube body and the distal portion of the proximal shaft may be as shown in FIGS. 10 and 11. In this embodiment, as shown in FIGS. 10 and 11, a proximal shaft 102, like the proximal shaft 2 in the above-described embodiment, includes a main body portion 121, a distal portion 122 smaller in diameter (or thinner) than the main body portion 121 and entering into the lumen 145 of a connection tube portion 104, and a proximal shaft inclined portion 123 connecting the main body portion 121 and the distal portion 122 to each other. The length of the distal portion 122 is preferably about 3 to 15 mm. The length of the inclined portion 123 in the axial direction is preferably about 2 to 10 mm.

In this embodiment, the distal portion 122 of the proximal shaft 102 is formed in a trough shape as if it were obtained by extending only a part of the main body portion 121 of the proximal shaft 102 in the axial direction as shown in FIGS. 10 and 11. The size of the arc formed in the cross-section obtained by cutting the distal portion 122 in the direction orthogonal to the axial direction of the distal portion 122 is preferably about $1/16$ to $1/2$ times the size of the circle formed in the cross-section of the main body portion 121. The distal portion 122 is not limited to one in which the trough shape is curved in the direction of the center axis of the shaft 102. The distal portion 122 may be trough-shaped so that it curves in the direction opposite to the direction of the center axis of the shaft 102 or in a flat plate-like shape.

In addition, the proximal shaft inclined portion 123 is formed to slant against or be inclined with respect to the center axis of the proximal shaft 102, over the range from the distal end of the main body portion 121 to the proximal end of the distal portion 122. In this version of the proximal shaft 102, the proximal shaft inclined portion 123 is in a form obtained by obliquely cutting out the proximal shaft 102 over a predetermined length, with the thus cut-out inclined portion constituting a communication portion for providing communication between a proximal shaft lumen 120 and a connection tube lumen 145. In other words, a distal portion of the proximal shaft 2 is in the form obtained by cutting out the proximal shaft 102 over a predetermined length and a predetermined width in the axial direction, the proximal shaft inclined surface 123 is in the form obtained by obliquely cutting out the proximal shaft 102 over a predetermined length, and the thus cut-out inclined portion constitutes the communication portion for communicating the proximal shaft lumen 120 and the distal shaft lumen.

The distal portion of the proximal shaft 2 may be cut into a shape in which the width of the distal portion is reduced toward the distal side.

In this embodiment, the connection tube portion 104 is in the form as shown in FIG. 10. The connection tube portion 104 is provided at its distal portion with a fixing portion 141 fixed to the outer tube 8, with a part of the side wall of the connection tube portion 104 on the proximal side relative to the fixing portion 141 including a fused portion 143 fused in a liquid-tight manner to a part of the side wall of a proximal portion of the inner tube 5. The connection tube portion 104 also includes a lumen change portion 146 contiguous with the fused portion 143 and extending toward the proximal side, a tubular portion 144 contiguous with the lumen change portion 146 and extending over a predetermined length, and a fixing portion 142 provided at the proximal end of the connection tube portion 104 for fixation to the proximal shaft 102. The proximal shaft inclined portion 123 of the proximal shaft 102 and the lumen change portion 146 of the connection tube portion 104 abut each other as shown in FIG. 10. In this embodiment, as shown in FIG. 10, the proximal shaft 102 is disposed inside the connection tube portion 104 so that the open side of its distal portion 122 is directed to the fused portion 143 and the inner tube 5. Incidentally, the distal portion 122 of the proximal shaft 102 may be in contact with or be slightly spaced from the inside surface portion of the connection tube portion 104 opposed to the fused portion 143.

Figure 12:
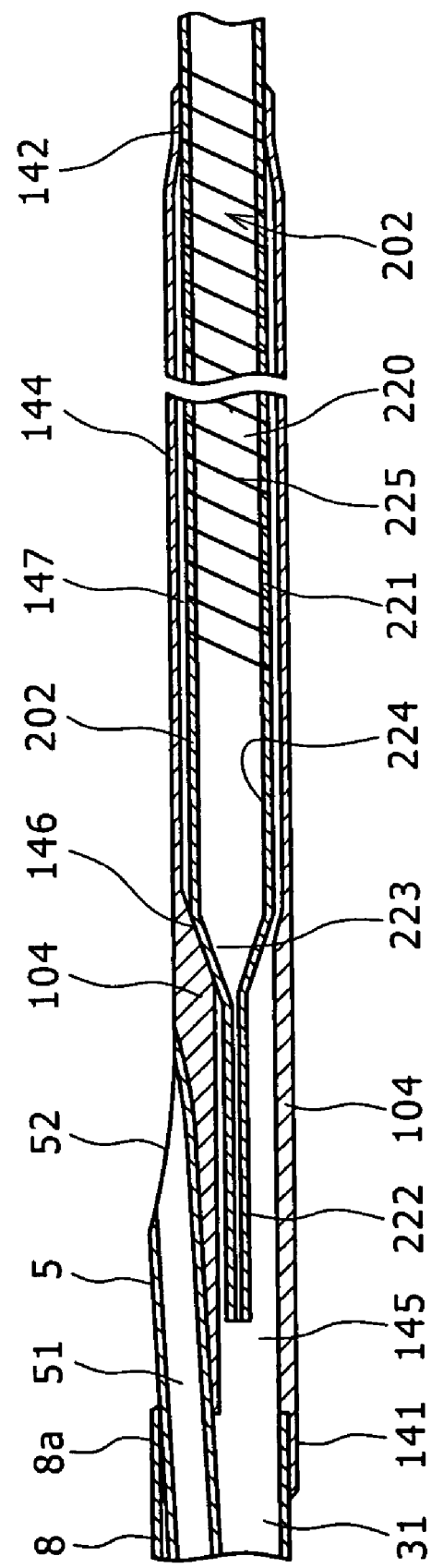
FIG. 12 is an enlarged cross-sectional view of the vicinity of a joint portion between a distal shaft and a proximal shaft in a further embodiment of the catheter according to the present invention.
Figure 13:
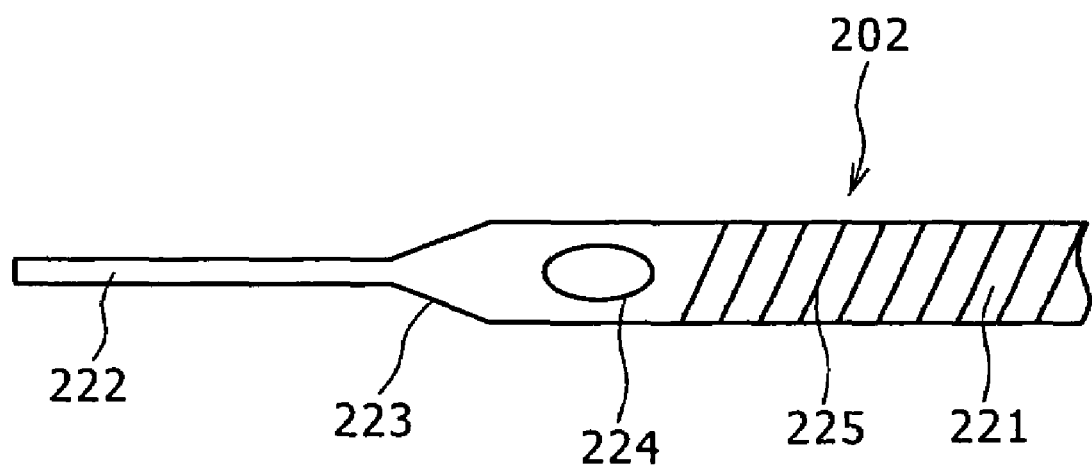
FIG. 13 is a perspective view of a distal portion of the proximal shaft used in the catheter shown in FIG. 12.

The connection tube portion and the distal portion of the proximal shaft may also be configured in the manner shown in FIGS. 12 and 13. The connection tube body 104 in this embodiment has the same configuration as that of the above-described connection tube body 104. As shown in FIGS. 12 and 13, a proximal shaft 202, like the proximal shaft 2 in the above-described embodiments, includes a main body portion 221, a distal portion 222 smaller in diameter (thinner) than the main body portion 221 and entering into the lumen 145 of the connection tube body 104, and a proximal shaft inclined portion 223 connecting the main body portion 221 and the distal portion 222. The proximal shaft inclined portion 223 of the proximal shaft 202 and a lumen change portion 146 of the connection tube portion 104 abut on each other. The length of the distal portion 222 is preferably about 3 to 15 mm. The length of the inclined portion 223 in the axial direction is preferably about 2 to 10 mm.

The distal portion 222 of the proximal shaft 202 is a small-diameter portion smaller in diameter than the main body portion 221 of the proximal shaft 202. The proximal shaft inclined portion 223 possesses a tapered shape reduced in diameter toward the distal portion 222 of the proximal shaft 202. In short, the distal portion 222 of the proximal shaft 202 possesses a hollow shape smaller in diameter than the main body portion 221 of the proximal shaft 202. The outside diameter of the distal portion 222 is preferably about 1/16 to 1/2 times the outside diameter of the main body portion 221. The proximal shaft inclined portion 223 is composed of a hollow tapered portion extending from the distal end of the main body portion 221 to the proximal end of the distal portion 222. The proximal shaft 202 is provided with a port 224 at the distal end of the main body portion 221 as generally indicated in FIG. 12 and more clearly shown in FIG. 13. It is to be understood that the port may also be provided in the inclined portion as in the proximal shaft shown in FIG. 15. The port may be a single port or may be a plurality of ports.

Figure 14:
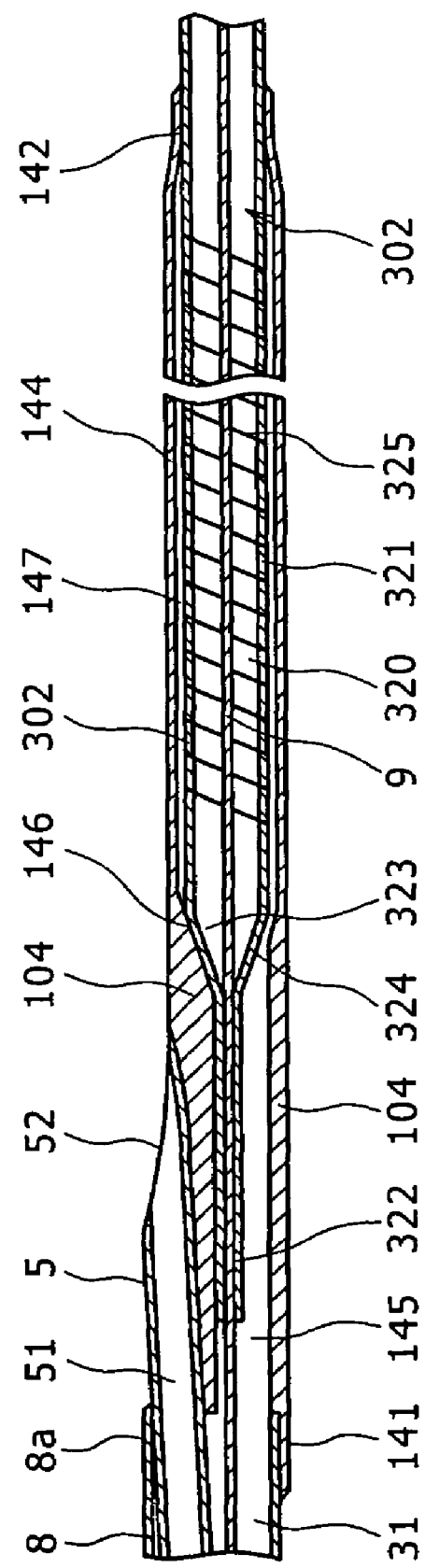
FIG. 14 is an enlarged cross-sectional view of the vicinity of a joint portion between a distal shaft and a proximal shaft in yet another embodiment of the catheter according to the present invention.
Figure 15:
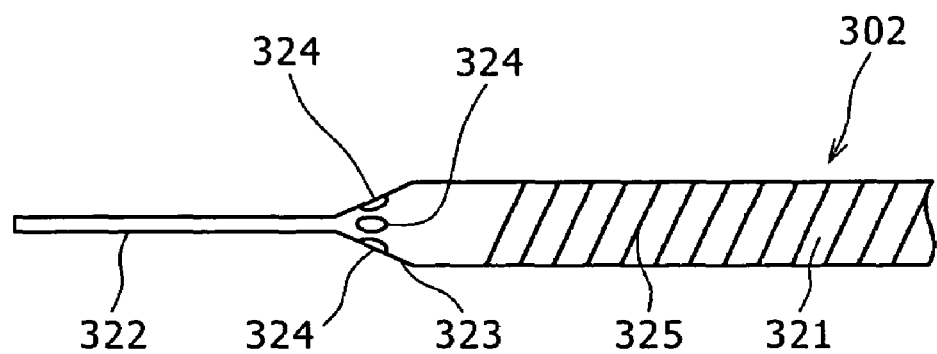
FIG. 15 is a perspective view of a distal portion of the proximal shaft used in the catheter shown in FIG. 14.

The connection tube body and the distal portion of the proximal shaft may be as shown in FIGS. 14 and 15. This embodiment is substantially the same as that shown in FIGS. 12 and 13, with the primary difference residing in that a rigidity-imparting body 9 penetrating through the proximal shaft is provided in the embodiment shown in FIGS. 14 and 15, and that the ports 324 are provided not in the main body portion but in the inclined portion 323 of the proximal shaft.

In this embodiment, the distal portion 322 of the proximal shaft 302 is formed in a hollow shape smaller in diameter to the main body portion 321 of the proximal shaft 302. The outside diameter of the distal portion 322 is preferably about 1/16 to 1/2 times the outside diameter of the main body portion 321. The proximal shaft inclined portion 323 of the proximal shaft 302 is composed of a hollow tapered portion extending from the distal end of the main body portion 321 to the proximal end of the distal portion 322. The proximal shaft 302 is provided with the ports 324 in its inclined portion 323 as shown in FIGS. 14 and 15. The ports 324 may be provided as a plurality of ports as in the proximal shaft shown in FIG. 15.

In all the above-described embodiments, the distal shaft is not limited to one with a coaxial tube structure of the inner tube and the outer tube. For example, a configuration may be adopted in which a guide wire lumen and a distal shaft lumen (balloon expanding lumen) are disposed in parallel to each other. In that case, the distal shaft is not provided with the inner tube but is provided with two lumens extending in parallel to each other.

Now, referring to FIG. 16, an example of a method of manufacturing a catheter according to the present invention will be described. Generally speaking, the method of manufacturing a catheter comprises preparing a connection tube portion 4 of which at least a distal portion is formed of a thermoplastic resin, preparing an outer tube 8 of which at least a proximal portion is formed of a thermoplastic resin, and preparing an inner tube 5 of which at least a proximal portion is formed of a thermoplastic resin. The inner tube 5 is then disposed in the inside of the outer tube 8, with the proximal portion of the inner tube 5 exposed from or beyond the outer tube 8. The inner tube 5 and the distal portion of the connection tube portion 4 are disposed in a substantially side-by-side relationship at the proximal portion of the outer tube 8; forming a distal shaft 3 by fusing the outer tube 8, the inner tube 5 and the connection tube portion 4, disposed as above-mentioned, to each other at the distal portion of the connection tube portion 4 and forming a lumen change portion 46 reduced in lumen section toward the distal side on the lumen of the connection tube portion 4. A proximal shaft 2 is prepared which includes a main body portion 21, a distal portion 22 smaller in diameter (thinner) than the main body portion 21 and adapted to enter into the lumen of the connection tube portion 4, and a proximal shaft inclined portion 23 located between the main body portion 21 and the distal portion 22. The distal portion 22 of the proximal shaft 2 is inserted into a proximal portion of the distal shaft 3 so that the distal portion 22 of the proximal shaft 2 is located in the lumen of the distal shaft 3 (connection tube portion 4) and so that the proximal shaft inclined portion 23 abuts on the lumen change portion 46, and both the shafts are fixed.

More specifically, the method involves first carrying out preparation or fabrication of the outer tube 8, the inner tube 5 and the connection tube portion 4 each formed of a thermoplastic resin. Blank material tubes for the outer tube 8, the inner tube 5 and the connection tube portion 4 are prepared respectively, and are cut to desired lengths. Next, one end of the inner tube 5 is cut obliquely, and the overall length thereof is set to a predetermined length. In addition, a distal portion of the connection tube portion 4 is cut obliquely.

Figure 16:
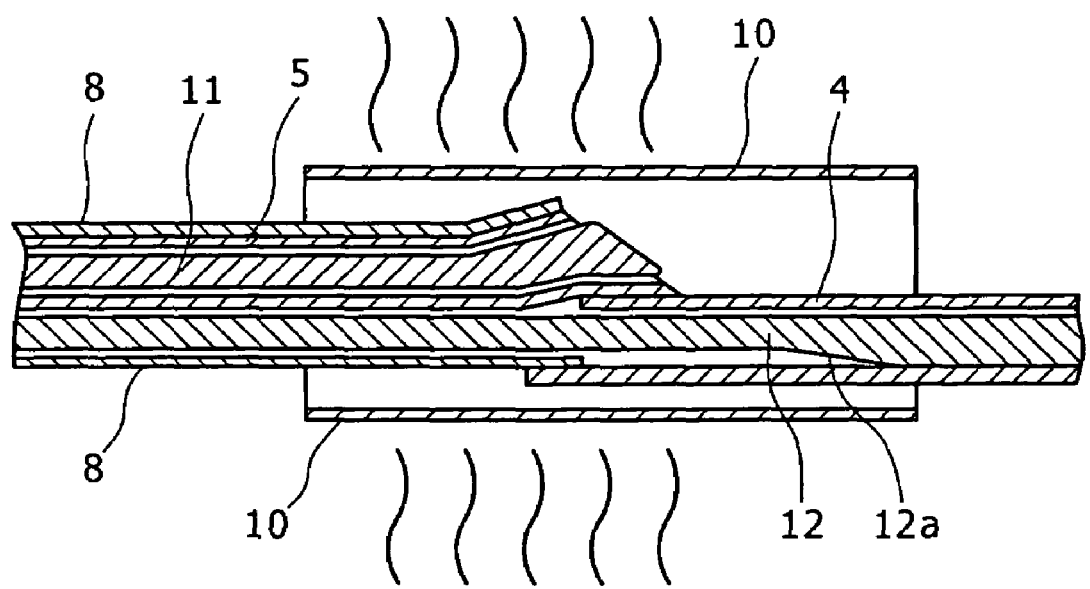
FIG. 16 illustrates a method of manufacturing a catheter according to the present invention.

Subsequently, a core metal 11 is inserted into the inner tube 5, a proximal portion of the inner tube 5 is set into a curved shape as shown in FIG. 16, and the inner tube 5 is inserted into the outer tube 8 together with the core metal 11 and is so disposed that the obliquely cut end of the inner tube 5 comes to the proximal end of the outer tube 8 or is slightly exposed or extended beyond the proximal end of the outer tube 8.

Next, the connection tube portion 4 with a core metal 12 inserted therein is so disposed as to be substantially side by side with the inner tube 5, in the vicinity of the proximal end of the outer tube 8 in which the inner tube 5 is disposed as above-mentioned. This step may be carried out before, or simultaneously with, the step of disposing the inner tube 5 inside the outer tube 8. The condition where the above steps or operations have been carried out is shown in FIG. 16. As shown in FIG. 16, the core metal 12 inserted in the connection tube portion 4 has an inclined surface portion 12a for forming the lumen change portion 46. It is to be understood that the lumen change portion 46 may be formed without using such a core metal by carrying out a fusing step as described later through the use of a heat-shrinkable tube shorter than the connection tube portion 4 so that the lumen of that portion of the connection tube portion 4 which protrudes out of or beyond the heat-shrinkable tube is left broad whereas the part of lumen located within the heat-shrinkable tube is narrowed through thermal deformation.

After the above-mentioned steps, a fusing operation is carried out involving heating a distal portion of the connection tube portion 4, a proximal portion of the outer tube 8 and a proximal portion of the inner tube 5 to fuse them to each other. As shown in FIG. 16, the region ranging from the proximal portion of the outer tube 8 and beyond the inclined surface portion 12a of the core metal 12 inserted in the connection tube portion 4 is enveloped by the heat-shrinkable tube 10, and the region is heated together with the heat-shrinkable tube 10, whereby the heat-shrinkable tube 10 is shrunk into close contact with the joint portion. Further heating is conducted, whereby the distal portion of the proximal shaft 2, the proximal portion of the outer tube 8 and the inner tube 5 are fused to each other, and the lumen change portion 46 reduced in lumen section toward the distal side is formed in the lumen of the connection tube portion 4.

The heating temperature in the fusing step is not less than the melting point of the material forming the connection tube portion 4. The heat-shrinkable tube 10 is produced by forming a tube smaller in inside diameter than the diameter of the joint portion of the inner tube 5, outer tube 8 and connecting tube portion 4, and broadening the tube in the radial direction. Examples of the material which can be used for forming the heat-shrinkable tube 10 include polyolefins such as polyethylene, polypropylene, etc., EAA (ethylene-acrylic acid copolymer), EVA (ethylene-vinyl acetate copolymer), silicone resins, and fluoro-resins. Particularly, a material incompatible with the materials used for forming the distal shaft, the inner tube, and the connection tube portion is used. After the fusing of the joint portion is completed, the heat-shrinkable tube is removed. As a result, the distal shaft 3 is formed.

Then, a proximal shaft 2 is prepared which includes a main body portion 21, a distal portion 22 smaller in diameter than the main body portion 21 and capable of entering into or being positioned in the lumen of the connection tube portion 4, and the proximal shaft inclined portion 23 located between the main body portion 21 and the distal portion 22. Subsequently, the distal portion 22 of the proximal shaft 2 is inserted into a proximal portion of the distal shaft 3 so that the distal portion 22 of the proximal shaft 3 is located inside the lumen of the distal shaft 3 (connection tube portion 4) and so that the proximal shaft inclined portion 23 abuts on the lumen change portion 46, and thereafter both the shafts are fixed. This fixation can be carried out by thermal fusing, by use of an adhesive, or the like method.

Further, in the case where the catheter is provided with a balloon 6 as shown in FIGS. 1 and 9, a balloon attaching operation is carried out for attaching a distal portion 6a of the balloon 6 to a distal portion of the inner tube 5 and attaching a proximal portion 6b of the balloon 6 to a distal portion of the outer tube 8. The balloon attaching operation is carried out by fusing (specifically, thermal fusing, high-frequency fusing, ultrasonic fusing), adhesion, ligation using a ligature, or the like method. Furthermore, in the case where the catheter is provided with contrast markers 17 and 18 as shown in FIG. 8, markers are attached before the balloon attaching operation.

Then, a hub 7 is attached to the proximal end of the proximal shaft 2.

The principles, preferred embodiments and manners of manufacture of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A catheter comprising:
a distal shaft;
a proximal shaft having a distal portion inserted and fixed in the distal shaft;
the distal shaft comprising a guide wire lumen and a distal shaft lumen, the guide wire lumen extending in a longitudinal direction of the distal shaft and communicating with a guide wire insertion port at a proximal portion of the distal shaft, the distal shaft lumen extending in the longitudinal direction of the distal shaft and communicating with a proximal shaft lumen formed inside the proximal shaft;
the proximal shaft comprising a main body portion, a distal portion smaller in outer dimension than the main body portion and entering into the distal shaft lumen, and a proximal shaft inclined portion located between the main body portion and the distal portion, the proximal shaft inclined portion possessing an inclined surface;
the distal shaft lumen possessing a lumen change portion that is reduced in lumen cross-section in a direction toward a distal side of the distal shaft lumen, the lumen change portion possessing an inclined surface; and
the inclined surface of the proximal shaft inclined portion and the inclined surface of the lumen change portion axially overlapping and directly abutting on each other so that a pushing force applied to the main body portion of the proximal shaft is transmitted to the distal shaft through the abutting proximal shaft inclined portion and lumen change portion,
wherein the lumen change portion is disposed proximally of a proximal-most portion of the guide wire insertion port, and
wherein the proximal shaft, including the inclined portion, is formed of metal.

2. The catheter as set forth in claim 1, wherein the distal shaft comprises an outer tube, an inner tube disposed in the outer tube, and a connection tube portion, the inner tube being fixed to the outer tube at a proximal portion of the inner tube and possessing the guide wire insertion port at the proximal portion of the inner tube, the connection tube portion being disposed side by side with the proximal portion of the inner tube, being fixed to the proximal portion of the inner tube and possessing a distal portion fixed in a liquid-tight manner to a proximal portion of the outer tube, the distal portion of the proximal shaft being inserted and fixed in the connection tube portion, the distal shaft lumen being defined between an inside surface of the outer tube or the connection tube portion and an outside surface of the inner tube, the lumen change portion being formed inside the connection tube portion, and the guide wire lumen being defined in the inner tube.

3. The catheter as set forth in claim 1, wherein the distal portion of the proximal shaft possesses a configuration in which the proximal shaft is cut out in an axial direction over a predetermined length and a predetermined width, the proximal shaft inclined portion possessing a configuration in which the proximal shaft is cut out obliquely over a predetermined length, and the cut-out inclined portion constituting a communication portion providing communication between the proximal shaft lumen and the distal shaft lumen.

4. The catheter as set forth in claim 1, wherein the distal portion of the proximal shaft possesses a trough shape in which only a part of the main body portion of the proximal shaft is extended in the axial direction, and the proximal shaft inclined portion is obliquely oriented relative to a center axis of the proximal shaft over a range from a distal end of the main body portion to a proximal end of the distal portion.

5. The catheter as set forth in claim 1, wherein the distal portion of the proximal shaft is a reduced outer dimension portion smaller in outer dimension than the main portion of the proximal shaft, and the proximal shaft inclined portion possesses a tapered shape which is reduced in outer dimension toward the distal portion of the proximal shaft.

6. The catheter as set forth in claim 1, wherein the proximal shaft inclined portion comprises a port providing communication between an inside of the proximal shaft and the distal shaft lumen.

7. The catheter as set forth in claim 1, wherein the proximal shaft main body portion comprises a port providing communication between an inside of the proximal shaft and the distal shaft lumen.

8. The catheter as set forth in claim 1, wherein the proximal shaft inclined portion is located on a proximal side of the guide wire insertion port.

9. The catheter as set forth in claim 1, wherein a distal end of the distal portion of the proximal shaft is located on the distal side relative to the guide wire insertion port.

10. The catheter as set forth in claim 1, wherein the distal portion of the main body of the proximal shaft is provided with a slit or a multiplicity of openings, and a proximal portion of the distal shaft envelopes the main body portion of the proximal shaft that is provided with the slit or multiplicity of openings, the proximal portion of the distal shaft being attached to the proximal shaft on a proximal side of the slit or multiplicity of openings.

11. The catheter as set forth in claim 10, wherein the slit is a spiral slit.

12. The catheter as set forth in claim 10, further comprising a gap between the main body portion of the proximal shaft provided with the slit or multiplicity of openings and the distal shaft enveloping the main body of the proximal shaft that is provided with the slit or multiplicity of openings.

13. The catheter as set forth in claim 1, further comprising a balloon having a distal portion and a proximal portion attached to a distal portion of the distal shaft, the balloon being expandable by a fluid introduced into the balloon by way of the distal shaft lumen.

14. A catheter comprising:
a distal shaft comprising a guide wire lumen and a distal shaft lumen which are separately disposed, the guide wire lumen extending longitudinally along at least a portion of the distal shaft and terminating at a guide wire insertion port at a proximal end of the guide wire lumen, the distal shaft lumen extending longitudinally along at least a portion of the distal shaft;
a proximal shaft fixed to the distal shaft, the proximal shaft comprising a proximal shaft lumen communicating with the distal shaft lumen;
the proximal shaft comprising a main body portion, a distal portion and a proximal shaft inclined portion located axially between the main body portion and the distal portion, the distal portion of the proximal shaft possessing an outer dimension that is reduced relative to the main body portion, the distal portion of the proximal shaft being positioned inside the distal shaft lumen, the proximal shaft inclined portion possessing an inclined surface that is inclined relative to a longitudinal axis of the proximal shaft;
the distal shaft lumen comprising a lumen change portion possessing an inclined surface; and
the inclined surface of the proximal shaft inclined portion and the inclined surface of the lumen change portion axially overlapping and directly abutting one another so that a pushing force applied to the main body portion of the proximal shaft is transmitted to the distal shaft through the abutting inclined surfaces of the proximal shaft inclined portion and the lumen change portion,
wherein the lumen change portion is disposed proximally of a proximal-most portion of the guide wire insertion port, and
wherein the proximal shaft, including the inclined portion, is formed of metal.

15. The catheter as set forth in claim 14, wherein the guide wire lumen is defined within an inner tube that is positioned within an outer tube, the inner tube being fixed to the outer tube at a proximal portion of the inner tube.

16. The catheter as set forth in claim 15, wherein the distal shaft comprises a connection tube portion disposed side by side with the proximal portion of the inner tube, the connection tube portion being fixed to the proximal portion of the inner tube and possessing a distal portion fixed in a liquid-tight manner to a proximal portion of the outer tube.

17. The catheter as set forth in claim 16, wherein the distal portion of the proximal shaft is positioned within and fixed to the connection tube portion, and the distal shaft lumen being defined between an inside surface of the outer tube or the connection tube portion and an outside surface of the inner tube.

18. The catheter as set forth in claim 14, wherein the distal portion of the proximal shaft is trough-shaped in which a circumferential extent of the distal portion of the proximal shaft is less than a circumferential extent of the main body portion of the proximal shaft.

19. The catheter as set forth in claim 14, wherein the distal portion of the proximal shaft possesses an outer dimension smaller than the outer dimension of the proximal shaft.

20. The catheter as set forth in claim 14, wherein the proximal shaft inclined portion comprises a port providing communication between an inside of the proximal shaft and the distal shaft lumen.

21. The catheter as set forth in claim 14, wherein the main body portion of the proximal shaft comprises a port providing communication between an inside of the proximal shaft and the distal shaft lumen.

22. The catheter as set forth in claim 14, wherein the proximal shaft inclined portion is located proximally of the guide wire insertion port.

23. The catheter as set forth in claim 14, wherein the distal end of the distal portion of the proximal shaft is located distally of the guide wire insertion port.

24. The catheter as set forth in claim 14, wherein the distal portion of the main body of the proximal shaft is provided with a slit or a multiplicity of openings, and a proximal portion of the distal shaft envelopes the main body portion of the proximal shaft that is provided with the slit or multiplicity of openings, the proximal portion of the distal shaft being attached to the proximal shaft on a proximal side of the slit or multiplicity of openings.

25. The catheter as set forth in claim 14, further comprising a balloon having a distal portion and a proximal portion, the proximal portion of the balloon being attached to a distal portion of the distal shaft, the balloon being expandable by a fluid introduced into the balloon by way of the distal shaft lumen.

* * * * *